United States Patent
Zasypkin et al.

(10) Patent No.: US 10,897,918 B1
(45) Date of Patent: Jan. 26, 2021

(54) EXTRUSION ENCAPSULATION WITH NARROW PARTICLE SIZE AND SHAPE DISTRIBUTION, HIGH SOLUBILITY, AND LOW SURFACE OIL

(71) Applicant: McCORMICK & COMPANY, INCORPORATED, Hunt Valley, MD (US)

(72) Inventors: Dmitriy Zasypkin, Sparks, MD (US); Shriram Paranjpe, Sparks, MD (US); Michael Reick, Sparks, MD (US); Chungsea Shen, Sparks, MD (US); Suzanne Johnson, Sparks, MD (US)

(73) Assignee: MCCORMICK & COMPANY, INCORPORATED, Hunt Valley, MD (US)

( * ) Notice: Subject to any disclaimer, the term of this patent is extended or adjusted under 35 U.S.C. 154(b) by 310 days.

(21) Appl. No.: 14/200,441

(22) Filed: Mar. 7, 2014

Related U.S. Application Data (60) Provisional application No. 61/798,390, filed on Mar. 15, 2013.

(51) Int. Cl.
*A23L 1/00* (2006.01)
*A23L 1/22* (2006.01)
*A61K 9/48* (2006.01)

(52) U.S. Cl.
CPC ......... *A23L 1/0029* (2013.01); *A23L 1/22016* (2013.01); *A61K 9/4816* (2013.01)

(58) Field of Classification Search
CPC ................................ A23L 27/72; A23L 19/01
See application file for complete search history.

(56) References Cited

U.S. PATENT DOCUMENTS

| | | | |
|---|---|---|---|
| 5,601,865 A | 2/1997 | Fulger et al. | |
| 5,603,971 A | 2/1997 | Fulger et al. | |
| 5,897,897 A | 4/1999 | Porzio et al. | |
| 6,187,351 B1 | 2/2001 | Porzio et al. | |
| 6,607,771 B2 | 8/2003 | Benczedi et al. | |
| 6,790,453 B2 | 9/2004 | Porzio et al. | |
| 7,488,503 B1 | 2/2009 | Porzio et al. | |
| 8,257,738 B2 | 9/2012 | Porzio et al. | |
| 2002/0189493 A1* | 12/2002 | Porzio | A01N 25/26 106/135.1 |
| 2003/0161884 A1* | 8/2003 | Rosenberg | A61K 9/1617 424/486 |
| 2005/0220981 A1* | 10/2005 | Renz | A23F 3/405 426/658 |
| 2009/0011097 A1* | 1/2009 | Koefod | A23B 4/0235 426/335 |
| 2011/0256199 A1 | 10/2011 | Zasypkin | |
| 2012/0027866 A1 | 2/2012 | Gregson et al. | |
| 2013/0243851 A1 | 9/2013 | Zasypkin et al. | |

OTHER PUBLICATIONS

U.S. Appl. No. 14/841,482, filed Aug. 31, 2015, Zasypkin.
U.S. Appl. No. 14/218,400, filed Mar. 18, 2014, Zasypkin, et al.
U.S. Appl. No. 13/828,533, filed Mar. 14, 2013, US2013/0243851 A1, Zasypkin, et al.
U.S. Appl. No. 13/087,732, filed Apr. 15, 2011, US2011/0256199 A1, Zasypkin.

* cited by examiner

*Primary Examiner* — Kyle A Purdy
(74) *Attorney, Agent, or Firm* — Greenblum & Bernstein, P.L.C.

(57) ABSTRACT

A glassy, particulate, melt extrusion encapsulation composition and a process of making the composition are described. The encapsulation composition is highly soluble in aqueous systems, has a low level of encapsulate on the surface of the particles, and has a narrow particle size and shape distribution. Food systems containing the encapsulation composition are also described.

29 Claims, 3 Drawing Sheets

FIGURE 1
DSC

FIGURE 2
DSC

EXTRUSION ENCAPSULATION WITH NARROW PARTICLE SIZE AND SHAPE DISTRIBUTION, HIGH SOLUBILITY, AND LOW SURFACE OIL

BACKGROUND OF THE INVENTION

Field of the Invention

The present invention relates to encapsulation compositions in a glassy state in which an encapsulate is encapsulated in a glassy matrix by a process known as melt extrusion. Melt extrusion should be distinguished from numerous drying processes including spray-, freeze-, tray-, or drum-drying, which could also lead to encapsulation of actives (encapsulants) in a glassy state. Melt extrusion generates the glassy state mainly by cooling the melted material while drying processes generate glassy products mainly by drying. In addition, melt extrusion could generate particles in a very broad range of the compositions and particle sizes. This difference leads to distinct and in many cases advantageous flavor encapsulation and flavor release properties of melt extrusion compositions. The compositions have very high true specific gravity, typically, above 1.4 g/cc, indicating very low porosity, uniform structure, resistance to mechanical stress, and thus effective protection of encapsulants.

More particularly, the present invention relates to flavor encapsulation compositions in which a flavoring agent is encapsulated by melt extrusion in a glassy matrix containing carbohydrates. More specifically, the present invention addresses the need for highly soluble compositions with a narrow particle size and shape distribution, carrying a high flavor load and yet having very low levels of flavor on the surface of the particles. Such compositions can consistently deliver actives including flavors in many applications requiring quick, controlled, and uniform release of the actives in final applications. The compositions also provide long shelf life and stability of actives due to a low level of actives, especially flavors, at the surface of the particles. The final applications could include food systems, personal care, or pharmaceutical compositions. The present invention also describes a method for preparing the extrusion encapsulation compositions and use of the compositions in final applications.

DISCUSSION OF THE BACKGROUND

The encapsulation of encapsulates is an area of active research. In particular, the encapsulation of such functional substances (actives) as flavoring agents, medications, pesticides, preservatives, vitamins and other dietary supplements is desired for a number of reasons. In the case of flavors, medications and pesticides, encapsulation may be desired to protect the actives and assure their controlled release. The encapsulation may be carried out to protect flavors and vitamins from air-oxidation and, thus, to extend shelf life of flavored compositions and vitamins. In the case of flavoring agents, personal care products, and pharmaceutical formulations, the encapsulation may be carried out to place the actives in an easily metered form which will protect the integrity of the composition and release the actives at a controllable event, such as the addition of water. In case of flavors, a defined flavor release assures the required time-intensity profile and consumer preferred functionality.

Various encapsulation processes are known to lead to a glassy state of the encapsulating matrix that serves as a flavor carrier. The advantages of retaining the glass form of the matrix include increased physical stability of the dense solid, reduced oxidation and loss of incorporated volatiles, and reduction of deleterious intermolecular reactions and oxidation. A glassy carrier can be made uniform with minimum imperfections such as pores or cracks for better protection of flavors and other encapsulants. The preparation of a solid in the glassy state depends upon both a matrix composition and a process used for generating an encapsulating material.

Current practical commercial processes leading to stable, dry flavors in the glassy state are limited in great part to spray drying and extrusion fixation. The former process requires emulsification or solubilization of a flavor in an aqueous carrier containing encapsulating solids, followed by rapid drying at a high temperature in a heated air flow and collection as a low-density bulk solid. The resultant moisture of the encapsulated compositions is in the range of 1%-4% assuring the glassy state at a temperature below 50° C. While spray drying accounts for many commercially encapsulated flavor materials, several limitations of the process are evident. Low molecular weight components of compounded or natural flavor mixtures generally exhibit a high vapor pressure could easily be lost or disproportionate during the process. The resultant encapsulated flavors are porous, powdery and difficult to handle. High surface area of the spray dried particles with the typical size below 100 microns could not in many cases assure a required extended shelf life. The final product, a dry, free flowing fine powder releases encapsulates rapidly upon hydration whether the rapid release is desired or not. The fine powder in many instances is prone to caking, difficult to handle or mix with other ingredients, and might present an explosion hazard.

Some other encapsulation processes may include freeze-drying, drum-drying and tray-drying. These processes have marginal significance due to a high processing cost, resulting porous structure of the material, and relatively poor protection of encapsulates, compared to spray drying and extrusion. The processes of drying are slow in the case of freeze- and tray-drying, and result in a weak glassy character of the material generated by slow drying rather than by quick cooling. Volatile flavor losses are very significant. Drum drying could be a fast process; however, loss of volatile components is very significant on the contact with a high temperature drying surface. All of the above processes other than spray-drying require a milling step further weakening the flavor. Considering the above limitations, melt extrusion offers significant advantages in flavor retention, protection of flavor integrity, and controlled release properties.

It is important to mention that melt extrusion is not a drying process. It generates glassy compositions by melting matrix components, followed by a quick cooling of the melt. Optionally, in-process or post-processing drying could be applied to further control moisture and other properties of compositions. Water or aqueous solutions used as a plasticizer are added in the amounts not preventing the formation of a glassy matrix with the glass transition temperature above ambient temperature. In other words, a quick cooling and optional drying of encapsulation compositions makes the compositions glassy with minimum water evaporation. Typically, water loss during cooling and drying could be from about 0.5% to about 5% based on the total weight of encapsulation composition. This distinguishes the melt extrusion process from spray-, drum-, or tray drying where a glassy matrix may be obtained mainly though evaporation of water from a slurry. Additional optional drying can be applied prior to or after cooling to further increase glass transition temperature of extruded compositions.

Many prior patents and patent applications describe a broad range of extrusion encapsulation compositions and processes leading to these compositions, for example, U.S. Pat. Nos. 5,603,971; 5,897,897; 6,187,351; 6,790,453; 7,488,503. U.S. Pat. Appl. No. 20120027866. These patents describe compositions where the melted matrix-flavor dispersions are extruded in the form of strands which are cooled and then milled. The milling process creates particles with a broad particle size distribution and high surface oil in case of flavors. The high surface oil results from a newly created high surface area of the particles generated during the milling process. To deal with this high surface oil the post-extrusion solvent washing was introduced as described, for example, in U.S. Pat. Appl. No. 20120027866. The broad particle size distribution resulted from milling could not provide consistent, fast, and controlled solubility of the particles and flavor release required in many applications such as seasonings, beverage blends, or baking applications. In addition, very fine particles resulting from the milling process could be lost, induce caking/hardening of the compositions, or are undesirable in the final applications for other reasons.

Another group of patents describes die-face cutting of the extruded melt when the melt exits from a die. A consistent linear speed of the extruded strands and constant rotation speed of a cutting knife affect particle size distribution of particles on cutting. For example, U.S. Pat. No. 5,601,865 does in general mention in the specification die-face cutting of the melted plastic strands (Col. 7). However, no such process has been claimed, or demonstrated in the examples, or specifically applied to highly soluble compositions containing significant amount of low molecular weight components such as crystalline sugars, polyols, or other carbohydrates. The patent does not teach low surface oil of the compositions. Instead, the patent teaches cooling the strands under ambient or an elevated pressure in a chamber prior to size reduction. A higher flavor retention of highly volatile flavors encapsulated and cooled under pressure is the primary claim of the '865 invention.

U.S. Pat. No. 6,607,771 describes a process for the preparation of a flavor or fragrance delivery system, wherein chopping the molten mass as it exits the die is described. While sugars and polyols are mentioned as a part of the continuous phase carrier there are no examples showing a composition containing low molecular weight sugars or polyols. Instead, described and claimed composition that may be made by the process in '771 is a composition "in a granular form having a glass transition temperature Tg which is essentially the same as that of the mixture." (Claim 1). The specification of '771 further elaborates on the mixture (col. 4) of a flavor or fragrance compound, a carbohydrate matrix, and a low amount of water "added to the mixture to guarantee that the glass transition temperature Tg of the resulting mixture corresponds to and is substantially the same as that of the desired Tg value of the final product." Such a requirement excludes compositions containing significant amounts of low molecular weight crystalline sugars or polyols that upon melting in the process effectively function as plasticizers in highly soluble compositions and reduce Tg of the product as compared to Tg of the mixture prior to processing.

The high level of low molecular weight sugars or polyols is essential to fast and controlled release of actives from the extruded encapsulation compositions but has not been adequately described in the literature.

Important challenges for melt extrusion encapsulation are a high flavor load especially above 8% by weight; high and controlled solubility of the compositions assuring fast flavor release within 15 seconds to 2 minutes; low surface flavor of the encapsulation compositions, especially less than 0.1% of total flavor; narrow particle size and shape distribution; and storage stability of the compositions in terms of caking, clumping, and flavor degradation. Many of these challenges are conflict with each other. Indeed, high solubility in water does require the presence of a significant amount of low molecular weight (LMW) sugars or polyols, small particles, and a high surface area. The presence of these LMW components makes the melt very sticky at the exit of the die in the process of extrusion. Such a sticky melt is difficult to die-face cut while cutting is important for a narrow particle size distribution and low surface oil in case of flavors. Plus, a significant amount of LMW components may not support a high flavor load with a typical target above 8% of a flavor in the final encapsulation compositions. When combined, these challenges are unmet in the prior art. The requirements are critical for expected functionality of the compositions in many industrial applications. Therefore, there is a need to develop compositions and processes meeting all the above requirements at the same time.

SUMMARY OF THE INVENTION

Accordingly, it is one object of the present invention to provide novel encapsulation compositions.

It is another object of the present invention to provide novel encapsulation compositions in the form of particles in which an encapsulate is encapsulated in a matrix which is stable in the glassy state at ambient temperatures.

It is another object of the present invention to provide novel encapsulation compositions in which an encapsulate is encapsulated at an increased level of up to 20% by weight of the encapsulation compositions.

It is another object of the present invention to provide novel, glassy encapsulation compositions that are highly and quickly soluble in polar solvents and especially in aqueous solutions and applications.

It is another object of the present invention to provide novel, glassy, flavor encapsulation compositions which exhibit required controlled release functionality and provide flavor integrity in product applications.

It is another object of the present invention to provide novel, glassy, flavor encapsulation compositions containing low surface flavor in order to prevent overall flavor degradation.

It is another object of the present invention to provide novel, glassy, flavor encapsulation compositions characterized by a narrow particle size and shape distribution.

It is another object of the present invention to provide novel processes for preparing such encapsulation compositions.

A further object of the present invention is to provide a food containing the extrusion encapsulation compositions of the present invention.

These and other objects, which will become apparent from the following detailed description, have been achieved by the inventor's discovery that it is possible to prepare by a melt extrusion process a glassy encapsulation composition in a granular form, which encapsulates up to 20% of an encapsulate, is highly and quickly soluble in aqueous solutions and other water containing systems, has a low level of encapsulates on the surface of the particles, and has particles within a narrowly defined particle size distribution.

Thus the present invention provides a particulate extrusion encapsulation composition in a glassy state, which is 1) soluble in aqueous systems within 15 seconds to 3 minutes under stirring or mixing, 2) has the level of encapsulate on the surface of the particles less than 1% based on the weight of the encapsulant, 3) has a narrow particle size and shape distribution, where each characteristic dimension of 90% of the particles by weight does not deviate by more than 30% from the mean value of that characteristic dimension; and comprising:

(A) encapsulate, encapsulated in (B) a glassy matrix comprising one or more matrix components, and one or more plasticizers;

wherein said glassy matrix (B) comprises: 10-50% of at least one low molecular weight sugar, polyol, corn syrup solids, organic acid or a salt of an organic acid; 0 to 60% of at least one modified starch, and 0 to 60%, based on the total weight of said glassy matrix (B), of at least one maltodextrin, inulin, gum Arabic, larch gum, gelatin, hydrolyzed gelatin, dextrin, hydrogenated starch hydrolyzate, wherein the encapsulate (A) is present in the extrusion encapsulation composition in an amount of from 4% to 20% by weight, based on the total weight of the extrusion encapsulation composition;

wherein said extrusion encapsulation composition is prepared by a process comprising:

(i) mixing the matrix components of the glassy matrix (B), the encapsulate (A), and the plasticizer, thereby obtaining a blend;

(ii) in at least one extruder melting the blend, dispersing the encapsulate in the melted blend to form a viscous dispersion, and cooling the viscous dispersion in the extruder or in a combination of extruders;

(iii) shaping, extruding and die-face cutting said viscous dispersion, thereby obtaining said extrusion encapsulation composition, wherein said encapsulate (A) is encapsulated in the glassy matrix (B), (iv) optionally drying the extruded encapsulation composition, and (v) further cooling the encapsulation composition.

Further, the present invention provides a process of making A particulate extrusion encapsulation composition in a glassy state, which is 1) soluble in aqueous systems within 15 seconds to 3 minutes under stirring or mixing, 2) has the level of encapsulate on the surface of the particles less than 1% based on the weight of the encapsulant, 3) has a narrow particle size and shape distribution, where each characteristic dimension of 90% of the particles by weight does not deviate by more than 30% from the mean value of that characteristic dimension; and comprising:

(A) encapsulate, encapsulated in (B) a glassy matrix comprising one or more matrix components, and one or more plasticizers;

wherein said glassy matrix (B) comprises: 10-50% of at least one low molecular weight sugar, polyol, corn syrup solids, organic acid or a salt of an organic acid; 0 to 60% of at least one modified starch, and 0 to 60%, based on the total weight of said glassy matrix (B), of at least one maltodextrin, inulin, gum Arabic, larch gum, gelatin, hydrolyzed gelatin, dextrin, hydrogenated starch hydrolyzate, wherein the encapsulate (A) is present in the extrusion encapsulation composition in an amount of from 4% to 20% by weight, based on the total weight of the extrusion encapsulation composition;

wherein said extrusion encapsulation composition is prepared by a process comprising:

(i) mixing the matrix components of the glassy matrix (B), the encapsulate (A), and the plasticizer, thereby obtaining a blend;

(ii) in at least one extruder melting the blend, dispersing the encapsulate in the melted blend to form a viscous dispersion, and cooling the viscous dispersion in the extruder or in a combination of extruders;

(iii) shaping, extruding and die-face cutting said viscous dispersion, thereby obtaining said extrusion encapsulation composition, wherein said encapsulate (A) is encapsulated in the glassy matrix (B), (iv) optionally drying the extruded encapsulation composition, and (v) further cooling the encapsulation composition.

DETAILED DESCRIPTION OF THE PREFERRED EMBODIMENTS

The inventors have discovered that it is possible to prepare by a melt extrusion process a glassy encapsulation composition in the form of particles, which encapsulates up to 20% of an encapsulate, is soluble in aqueous solutions and other water containing systems within 15 second to 3 minutes under stirring or mixing, has a level of encapsulates on the surface of the particles less than 1% of the total weight of the encapsulate, comprised of the particles with a narrow particle size distribution defined here below, and is stable during storage over at least six months when packaged. More specifically, the inventors discovered that it is possible to achieve all the above characteristics of the encapsulation composition by balancing the encapsulation composition and the extrusion process. The most challenging part in the development of highly soluble compositions is the need to incorporate more than 10%, preferably more than 20%, and most preferably more than 30% of low molecular weight sugars or polyols in a combination with other components in the carrier that ideally should also have a relatively low molecular weight (LMW) for increased solubility. The initially crystalline LMW components upon melting in the presence of water form low viscosity melt that effectively reduces viscosity of the entire melted composition. Thus, LMW components function as a plasticizer. This contributes to reduced elasticity of the melt, resulting to an increased stickiness and smearing during cutting.

Figure 1:
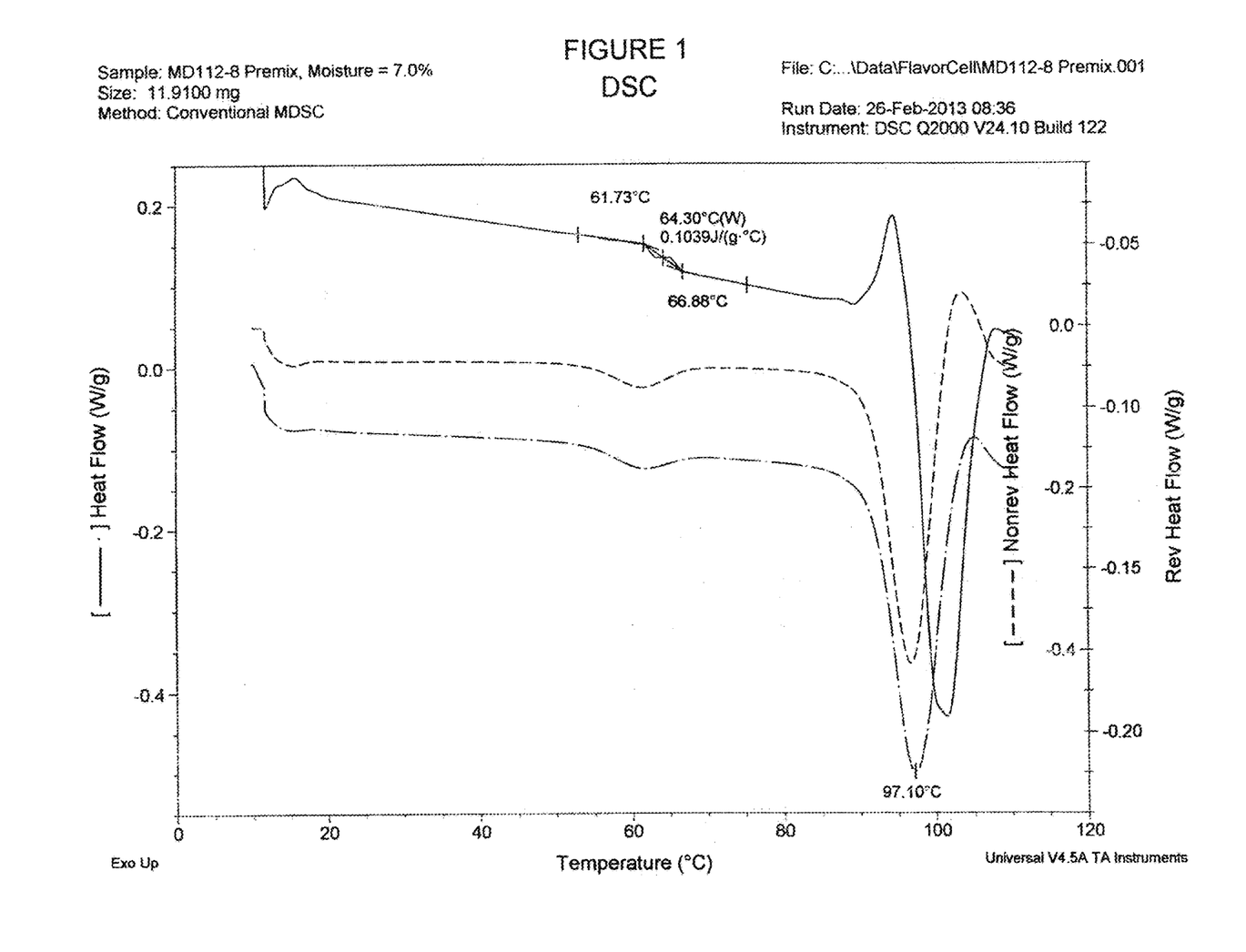
FIG. 1 is a MDSC graph showing thermal transitions during heating of a matrix dry blend comprising, based on the total weigh of the matrix composition, 30% maltodextrin 18DE, 40% OSAN-modified starch, and 30% trehalose dehydrate. The blend contains 7% moisture. Two thermal transitions were identified: a glass transition at 64.9° C. (reversing heat flow plot: solid line) and a melting transition at 97° C. (total heat flow plot: dotted dash line). The glass transition is typical for dried maltodextrins and modified starches while the melting transition is the melting trehalose dehydrate.
Figure 2:
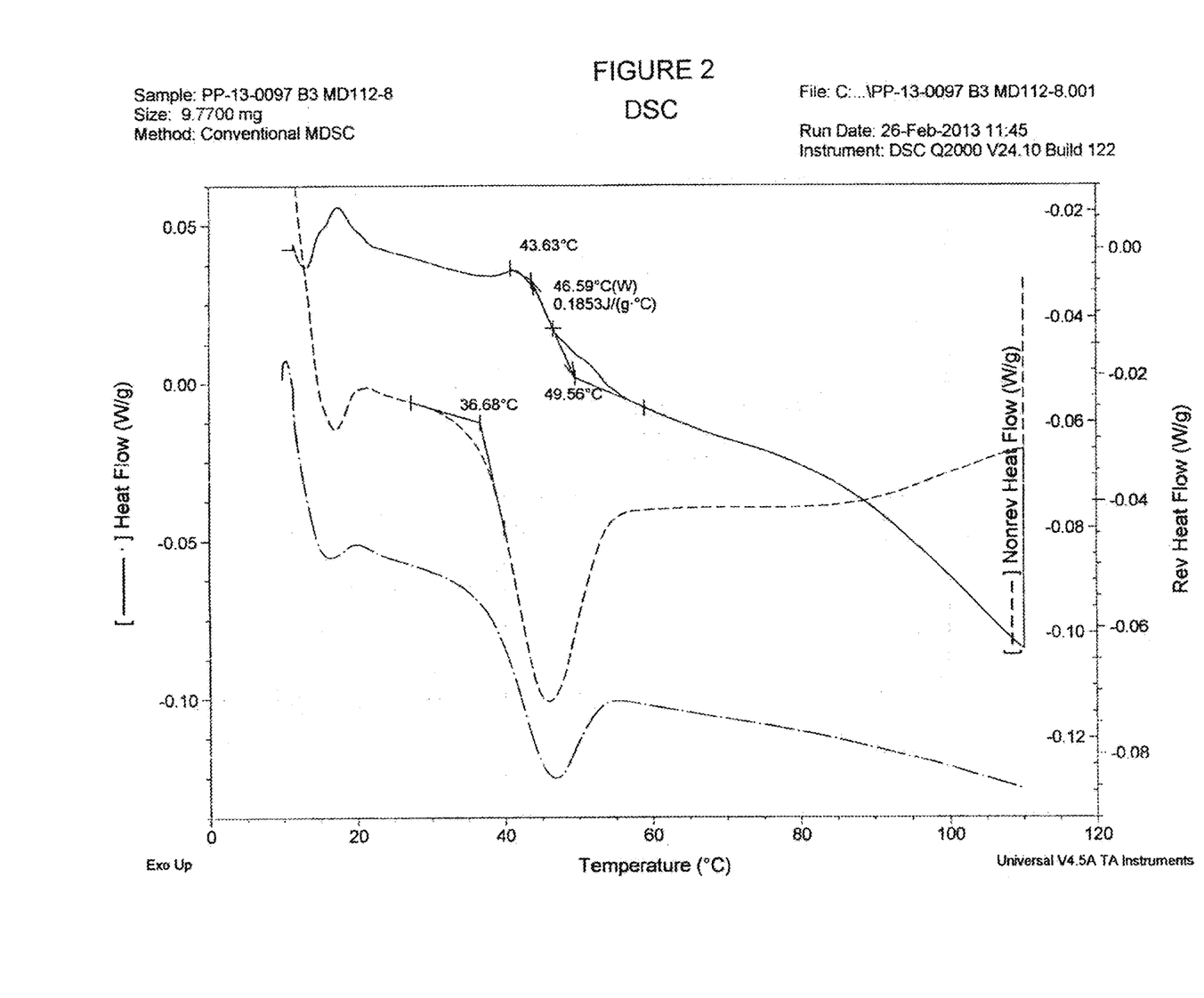
FIG. 2 is a MDSC graph showing thermal transitions during heating of a final encapsulation composition prepared with the matrix comprising of, based on the total weigh of the matrix composition, 30% maltodextrin 18DE, 40% OSAN-modified starch, and 30% trehalose dehydrate, and 10% orange Valencia flavor, using the process described in the Examples. The blend contains 5.1% moisture. A glass transition was identified at 46.4° C. (reversing heat flow: solid line). The glass transition is typical for extrusion encapsulation compositions. It shows that even at lower moisture of the encapsulation composition as compared to that of the original matrix blend the glass transition temperature (Tg) of the encapsulation composition is lower by 18.5° C. than Tg of the matrix blend. No melting transition appears on the graph showing true glassy state of the encapsulation composition (total heat flow: dotted dash line).

The inventors demonstrated that while the LMW components of the compositions function as a plasticizer effectively reducing glass transition temperature (Tg) it is possible to prepare glassy encapsulation compositions with Tg above 25° C., preferably above 35° C., and even more preferably above 45° C. It is important to note that Tg of the final encapsulation composition is not the same as that of the initial mixture of the components prior melting and extrusion (FIGS. 1 and 2). First of all, in some cases an additional plasticizer is added to the initial dry blend. This plasticizer could be water, glycerin, propylene glycol, an organic acid, a salt of an organic acid, or aqueous solutions of LMW carbohydrates. Even if we consider the plasticizer as a part of the initial mixture, Tg of the initial mixture is not the same as Tg of the encapsulation composition for at least two reasons. First of all, LMW sugars, polyols, and other carbohydrates in the matrix are in a crystalline or in a partially crystalline form (FIG. 2). These crystalline components are not in a glassy state and need to be melted to be a part of the glassy encapsulation composition. Only amorphous parts of the initial blend will exhibit a single or multiple glass transition temperatures. The crystalline components are characterized by a melting transition and once melted will contribute to Tg of the encapsulation composition typically by lowering it due to their LMW (FIGS. 1 and 2). Secondly, glass transition is a function of cooling and/or drying of the melted composition. By definition, glassy state of a material is a result of its supercooling. Therefore, the way the final melt is cooled or dried does contribute to glassy properties of the final composition, including glass transition temperature. The quicker cooling or drying of the melt, the greater degree of supercooling and the higher Tg.

The inventors also discovered that the LMW components of the encapsulation composition while contributing to plastification of the melt also allow for reduction of other plasticizers. This is critical to assuring a high Tg at the levels of LMW components in the matrix above 10% by weight of the matrix. In other words, the LMW components reduce Tg and also reduce viscosity of the melt. It is the reduction in viscosity that allows for reduction of the amount of other plasticizers, e.g. water. The reduction of water or other liquid plasticizers compensates for lower Tg resulted from a large amount of LMW components, thus satisfying the requirement for Tg of the encapsulation composition to be above 25° C. preferably above 35° C., and even more preferably above 45° C. Once the encapsulation composition is in the glassy state, the molecular mobility of matrix components is greatly reduced and they do not exhibit a significant recrystallization (FIG. 1 and FIG. 2).

The solubility of the compositions may be defined and measured as the time to completely solubilize the encapsulation composition in water or in an aqueous system at a specified temperature and under defined mixing conditions. Also included is the definition of solubility where above 30%, preferably above 50% by weight of the encapsulation composition is dissolved or disintegrated to release an encapsulant within the timeframe defined below. The aqueous system could be a beverage, a sauce, dough, a chewing gum, or any other system containing water or exposed to water whether in processing, in a final application, or during chewing and mastication. More specifically, also included in the aqueous systems are the food systems where the encapsulation composition of the present invention is not exposed to high moisture during processing of such food systems. In this case the encapsulation composition may not be dissolved or is only partially dissolved in the food system during processing but is dissolved during chewing or mastication of such food system. For example, the encapsulation composition could be applied topically to bread dough before baking, survive the baking process, and release the encapsulated flavor during consumption. Depending on the test system or application the solubility time for the composition may be from 10 seconds to 5 minutes, more preferably from 20 seconds to 2 minutes, most preferably 30 seconds to 1 minute. One test that may be used to characterize the solubility of particles employs solubilization of 0.5 g of the particles of the encapsulation compositions in 150 g of water at 50° F. under constant stirring with a spoon or a stirring blade at about 120 spins or rotations per minute. Then the minimum time required to completely solubilize the particles can serve as a measure of the solubility rate. The complete solubility is determined when the particles are no longer visible at the bottom of the glass after stirring of the solution stops. A similar method can be developed for any application of interest.

Figure 3A:
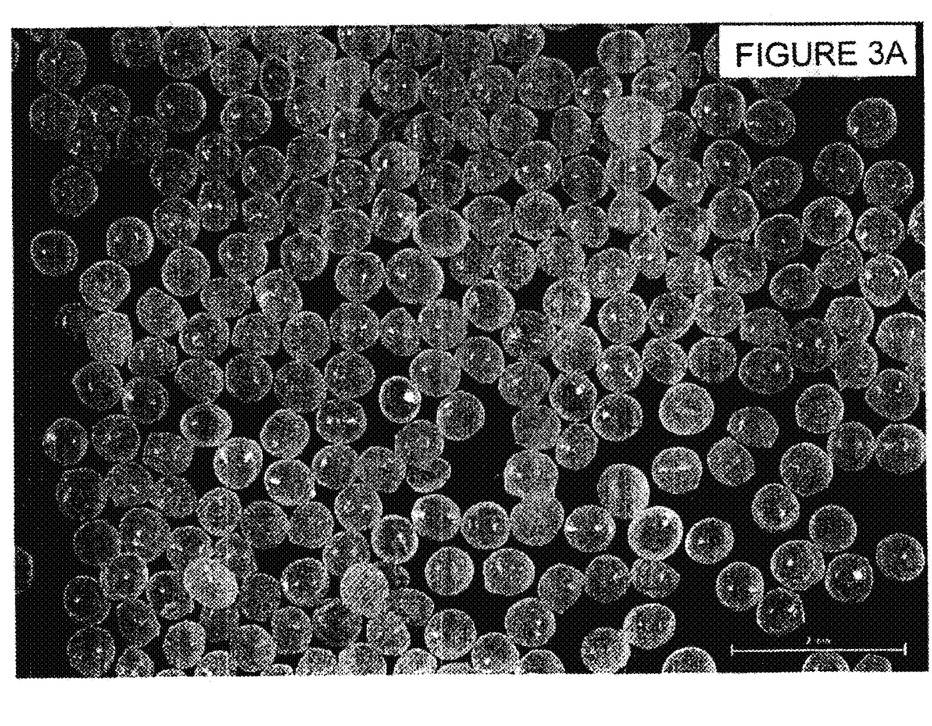
FIG. 3A shows a typical narrow particle size and shape distribution of the encapsulation composition of the present invention. Particles are cut at a fixed rotation speed of the knife and at a fixed linear speed of strands coming out of the extruder die.

Clean and robust die-face cutting is yet another requirement needed to provide a narrow particle size and shape distribution critical to fast or controlled release of encapsulants in target applications. The inventors have surprisingly discovered that stickiness and excessive fluidity of highly soluble compositions can be controlled with the right balance of the encapsulation composition and by additional cooling of the melt in an extruder prior to die-face cutting. A cooling jacket of a cooling zone of an extruder or an assembly of extruders has been demonstrated to be important to control cutting of encapsulation compositions containing a high level of LMW components. In this case cooling is provided at the surface where the highest shear rates are applied to the melt. This surface is the internal surface of the barrel of an extruder. The high shear rates generate significant heat and temperature increase during mixing and conveying the melt along the extruder. Thus, effective cooling is provided right at the surface where a significant heat is generated. In this way, the temperature profile and viscosity is more even across the flow of the melt. In turn, this more uniform temperature and viscosity profile of the melt across the flow leads to more uniform linear speed of strands of the melt being extruded through the die holes. The result is a narrow or narrowly defined particle size distribution when the strands are cut by a cutter at the die face (FIG. 3A). The additional cooling is also important for an increased elasticity of the melt and helps to reduce stickiness of the melt and thus improve cutting.

A number of components added to the matrix (B) could help reduce stickiness of the melt during die-face cutting. These anti-sticking components could include but not limited to calcium, magnesium, sodium, or potassium salt of a fatty acid; mono-di-glycerides; silicon or titanium dioxide; propylene glycol monostearate; a lecithin, and saturated fats. Some starches, modified starches, and gums including xanthan gum, agar-agar, carrageenan, alginate, cellulose derivatives, and edible fibers could also assist in preventing stickiness of strands of a melted encapsulation composition during cutting.

The inventors demonstrated that particles can be prepared by die-face cutting in a wide range of specified sizes, from 0.1 mm to 7 mm depending on the die used in the extrusion process. Particles could be spherical, nearly spherical, halfspheres, rods, or flake-shaped at the other extreme of the spectrum. Depending on the shape of the die holes and the speed of the cutting knife the particles could have a variety of shapes and aspect ratios, including ones mimicking letters, logos, and familiar food shapes. More preferred target particle sizes are in the range between 0.3 mm and 0.9 mm. Particle size and shape have an effect on solubility, caking, and flavor stability. The smaller the particles and the less spherical they are in shape the faster is the solubility rate. The described die-face cutting can assure a narrow particle size and shape distribution (FIG. 3A). In one preferred embodiment the width of the distribution is such that 90% of the particles by weight do not deviate in size from the mean value by more than 50% of the mean value. In more preferred embodiment 90% of the particles by weight do not deviate in size from the mean value by more than 30% of the mean value. In yet more preferred embodiment 90% of the particles by weight do not deviate in size from the mean value by more than 20% of the mean value. For example, in this more preferred embodiment if the mean particle size is 500 microns then 90% of the particles by weight would have a size between 400 and 600 microns. If the shape of the particles is not spherical then the same specification may be applied to each characteristic dimension of the particles. For example, if the particles are cylindrical rods then 20% deviation is applied to each characteristic dimension, namely, to the length of the rods as well as to their diameter.

Figure 3B:
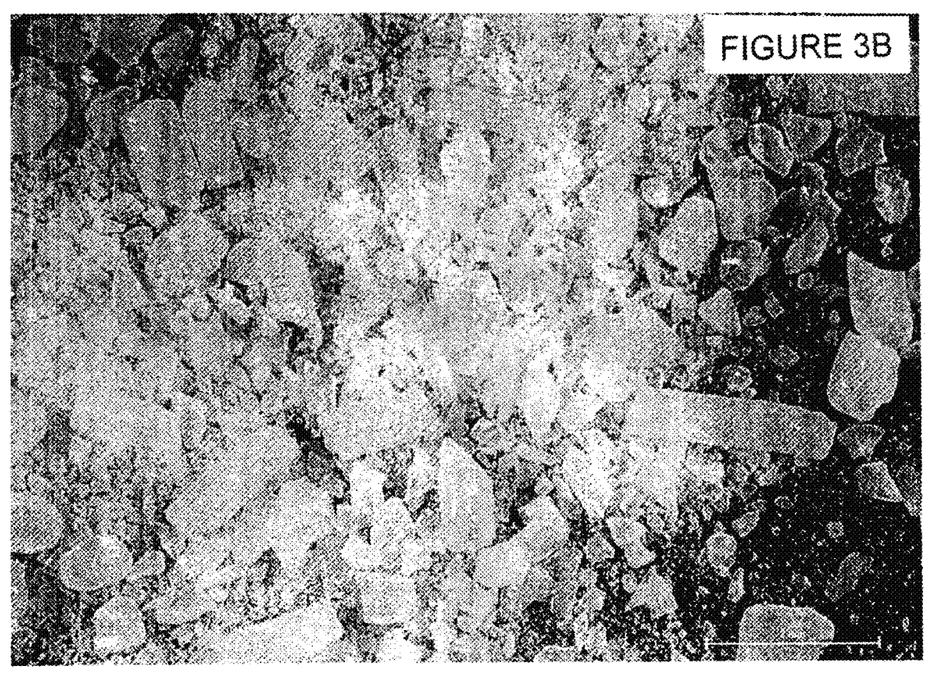
FIG. 3B shows a typical broad particle size and shape distribution of the encapsulation composition made by the same process as the encapsulation composition shown in FIG. 3A, except in this case the strands were extruded, cooled then milled through a grated sieve. This process also resulted to about 10% fines passing through the standard USS60 sieve.

The narrow particle size and shape distribution of the present invention as shown in FIG. 3A is in sharp contrast with a broad distribution generated by milling of cooled and glassy strands as shown in FIG. 3B. Milling creates dramatically broader particle size and shape distribution with a significant amount of fine particles usually referred to as fines. The fines have very high surface area, could have a high surface flavor, and could limit storage stability whether in terms of caking and clumping of the powder or flavor degradation.

The particle size and shape distribution may be measured or evaluated in a number of ways known in the art, including but not limited to the following methods: direct measurement with a caliper, sieve analysis, light scattering methods, microscopy, optical projection methods accompanied with image analysis. The particle size distribution may be defined as a distribution of particles by their size, surface area, weight, volume, color, or any other characteristic of interest.

The encapsulation composition is balanced in such a way that it can encapsulate up to 20% of an encapsulate, based on the total weight of encapsulation composition. In case of flavors the preferred flavor load is in the range from 5 to 15%, the most preferred is in the range from 7 to 12%. The encapsulates are typically dispersed in the carbohydrate carrier with the help of emulsifiers. The emulsifiers can be present in the encapsulate, in the matrix or in both. The emulsifiers could be of different nature: from lipid based emulsifiers to surface active biopolymers, to surface active saponins and other surface active natural extracts and ingredients. The emulsifiers or surface active components of the encapsulation composition assure effective emulsification or dispersion of encapsulants in the melted matrix. The presence of emulsifiers can also help control cutting of the melt, solubility of particles, residual flavor on the surface of particles, and controlled release of flavors.

As was discussed above, other critical properties of the encapsulation composition are a high solubility in aqueous systems and non-stickiness of the melt in the process of cutting. Yet another requirement to the composition is a low level of an encapsulate or encapsulates on the surface of particles, resulted from cutting of the extruded melt followed by optional drying and cooling. The inventors discovered that it is possible to minimize surface flavor down to less than 1% based on the total weight of the flavor in the encapsulation composition. The surface flavor needs to be minimized to prevent oxidation, loss, or other flavor degradation.

A number of ways have been found to minimize the surface flavor. The inventors discovered that die-face cutting of the hot melt creates hot surfaces which volatile flavors are evaporated from. Even though some part of a volatile flavor could be lost in this way, the resulting surface flavor is low. This helps protect flavor integrity in the final encapsulation composition and is applicable to many volatile encapsulants. Greater emulsifying capacity of the encapsulating matrix was also found important in reduction of surface flavors. Finally, cooling the melt in an extruder prior to cutting and cutting larger particles without compromising high solubility of the particles were factors in satisfying the requirement of low levels of encapsulants on the surface of particles. The surface flavor may be measured by a non-polar solvent extraction of the particles followed by GC analysis.

The inventors surprisingly discovered that it is possible to satisfy all the above requirements and generate a particulate extrusion encapsulation composition in a glassy state, which is 1) soluble in aqueous systems within 15 seconds to 3 minutes under stirring or mixing, 2) has the level of encapsulate on the surface of the particles less than 1% based on the weight of the encapsulant, 3) has a narrow particle size and shape distribution, where each characteristic dimension of 90% of the particles by weight does not deviate by more than 30% from the mean value of that characteristic dimension; and comprising:
    (A) encapsulate, encapsulated in (B) a glassy matrix comprising one or more matrix components, and one or more plasticizers;
    wherein said glassy matrix (B) comprises: 10-50% of at least one low molecular weight sugar, polyol, corn syrup solids, organic acid or a salt of an organic acid; 0 to 60% of at least one modified starch, and 0 to 60%, based on the total weight of said glassy matrix (B), of at least one maltodextrin, inulin, gum Arabic, larch gum, gelatin, hydrolyzed gelatin, dextrin, hydrogenated starch hydrolyzate,
    wherein the encapsulate (A) is present in the extrusion encapsulation composition in an amount of from 4% to 20% by weight, based on the total weight of the extrusion encapsulation composition;

wherein said extrusion encapsulation composition is prepared by a process comprising:
(i) mixing the matrix components of the glassy matrix (B), the encapsulate (A), and the plasticizer, thereby obtaining a blend;
(ii) in at least one extruder melting the blend, dispersing the encapsulate in the melted blend to form a viscous dispersion, and cooling the viscous dispersion in the extruder or in a combination of extruders;
(iii) shaping, extruding and die-face cutting said viscous dispersion, thereby obtaining said extrusion encapsulation composition, wherein said encapsulate (A) is encapsulated in the glassy matrix (B),
(iv) optionally drying the extruded encapsulation composition, and
(v) further cooling the encapsulation composition.

Further, the inventors surprisingly discovered an effective process of making a particulate extrusion encapsulation composition in a glassy state, which is 1) soluble in aqueous systems within 15 seconds to 3 minutes under stirring or mixing, 2) has the level of encapsulate on the surface of the particles less than 1% based on the weight of the encapsulant, 3) has a narrow particle size and shape distribution, where each characteristic dimension of 90% of the particles by weight does not deviate by more than 30% from the mean value of that characteristic dimension; and comprising:
(A) encapsulate, encapsulated in (B) a glassy matrix comprising one or more matrix components, and one or more plasticizers:
wherein said glassy matrix (B) comprises: 10-50% of at least one low molecular weight sugar, polyol, corn syrup solids, organic acid or a salt of an organic acid; 0 to 60% of at least one modified starch, and 0 to 60%, based on the total weight of said glassy matrix (B), of at least one maltodextrin, inulin, gum Arabic, larch gum, gelatin, hydrolyzed gelatin, dextrin, hydrogenated starch hydrolyzate,
wherein the encapsulate (A) is present in the extrusion encapsulation composition in an amount of from 4% to 20% by weight, based on the total weight of the extrusion encapsulation composition;
wherein said extrusion encapsulation composition is prepared by a process comprising:
(i) mixing the matrix components of the glassy matrix (B), the encapsulate (A), and the plasticizer, thereby obtaining a blend;
(ii) in at least one extruder melting the blend, dispersing the encapsulate in the melted blend to form a viscous dispersion, and cooling the viscous dispersion in the extruder or in a combination of extruders to form a melted dispersion;
(iii) shaping, extruding and die-face cutting said viscous dispersion, thereby obtaining said extrusion encapsulation composition, wherein said encapsulate (A) is encapsulated in the glassy matrix (B),
(iv) optionally drying the extruded encapsulation composition, and
(v) further cooling the encapsulation composition.

In one preferred embodiment, the inventors discovered that that it is possible to satisfy all the above requirements to the encapsulation composition by using a glassy matrix (B) that comprises: 20%-40% by weight, based on the total weight of said glassy matrix (B), of at least one low molecular weight sugar, polyol, corn syrup solids, organic acid or a salt of an organic acid, and 10%-60%, based on the total weight of said glassy matrix (B), of at least one modified starch, and 0 to 60% of at least one maltodextrin.

In yet another embodiment, an amount of the encapsulate (A) at the surface of the encapsulated composition is not greater than 1%, preferably, not greater than 0.1%, and more preferably, not greater than 0.01%, of the total amount of encapsulate (A) in the encapsulation composition.

In one embodiment the encapsulation composition is stable in a packaging as to caking, clumping, and flavor degradation for at least six months, preferably for at least one year, and most preferably over two years at ambient conditions.

In one embodiment, the extrusion encapsulation composition employs a glassy matrix comprising a modified starch, a plasticizer, and at least one of sucrose, maltose, trehalose, corn syrup solids, lactose, dextrose, xylose, fructose.

In one embodiment, the extrusion encapsulation composition employs a glassy matrix comprising a carbohydrate, and at least one of sucrose, maltose, trehalose, corn syrup solids, lactose, dextrose, xylose, fructose, and does not contain any added plasticizer.

In yet another embodiment, the encapsulation composition has a glass transition temperature of from 25° C. to 80° C.

In a different embodiment, the glassy matrix (B) comprises from 0.2% to 8% by weight, based on the total weight of said glassy matrix B, of an emulsifier.

The encapsulate can be at least one component selected from the group consisting of a flavor, a vitamin, a dietary supplement, a medication, a preservative, and a pesticide.

In one embodiment, the encapsulate is a flavor.

In another embodiment, the flavor is at least one flavor selected from the group consisting of a natural flavor, an oleoresin, an essential oil, a protein hydrolyzate, an aqueous reaction flavor, an artificial flavor, and a compounded flavor.

A plasticizer can be at least one plasticizer selected from the group consisting of water, glycerin, propylene glycol, an organic acid, a salt of organic acid, and a carbohydrate solution.

In one embodiment, shaping is performed by extruding and die-face cutting the melted mixture with a cutter to form particles, wherein said particles are dried and cooled.

The glassy extrusion encapsulation composition contains less than 12% water, preferably less than 8%, more preferably less than 5% water, and contains the encapsulate (A) in the range of from 0.01 to 20%, preferably from 0.5 to 12%, based on the total weight of the glassy extrusion encapsulation composition.

The modified starch can be at least one starch selected from the group consisting of n-octenylsuccinic anhydride modified starches (OSAN-starch). The starches may be concomitantly modified by dextrinization and chemically derivatized with n-octenylsuccinic acid anhydride. Alternatively, the starch may undergo initial chemical or enzymatic hydrolysis followed by the derivatization with n-octenylsuccinic acid anhydride.

Maltodextrins are also suitable carbohydrate food polymers. These polymers are derived from partially hydrolyzed forms of corn, rice, wheat, tapioca, or potato starches utilizing suitable acid or enzymatic catalysis. The maltodextrins are defined as having a dextrose equivalent (DE) of 20 or less. Particularly suitable maltodextrins are 5 DE, 10 DE, 11 DE, 15 DE, 18 DE, 19 DE maltodextrins.

Gums including but not limited to xanthan, carrageenan, alginate, pectin, guar gum, tara gum, agar-agar, modified celluloses, inulin could be used in small amounts typically not exceeding 10%, preferably not exceeding 5% based on the weight of matrix (B), to modulate solubility, cutting, and other properties of the encapsulation composition.

In one embodiment, the encapsulation composition contains 5 to 50% by weight, preferably 10 to 40% by weight, 15 to 30% by weight, or 20 to 30% by weight, based on the total weight of the glassy matrix, of at least one component selected from the group consisting of a low molecular weight sugar, a low molecular weight polyol, a corn syrup solid, an organic acid, a salt of an organic acid, and a mixture thereof. Examples of suitable sugars include mono- and disaccharides (including glucose, sucrose, maltose, fructose, galactose, ribose, xylose, lactose, cellobiose, and trehalose), invert syrups, molasses, and corn syrups. The preferred sugars are sucrose, maltose, dextrose, lactose, and trehalose. The sugars can be used singly or in a combination.

Polyols are a group of lower molecular weight ingredients known as polyhydric agents. Simple polyols include glycerin and propylene glycol that can be used as plasticizers. Examples of other polyols include erythritol, lactitol, mannitol, sorbitol, maltitol, isomalt, xylitol, hydrogenated corn syrups, hydrogenated glucose syrups, hydrogenated maltose syrups, and hydrogenated lactose syrups. The preferred polyols are mannitol, maltitol, and isomalt. The polyols can be used singly or in a combination. Suitable corn syrup solids have 24 to 42 DE.

The term encapsulate as used in this application, includes agents such as medications, pesticides, preservatives, vitamins, food acids, salts, flavors, perfumery chemicals and fragrances, food colorants both synthetic and natural, high intensity sweeteners, flavor adjuvants, and combinations thereof.

The term flavor includes spice oleoresins and oils derived from allspice, basil, *capsicum*, cinnamon, cloves, cumin, dill, garlic, marjoram, nutmeg, paprika, black pepper, rosemary and turmeric; essential oils such as anise oil, caraway oil, clove oil. *eucalyptus* oil, fennel oil, garlic oil, ginger oil, peppermint oil, onion oil, pepper oil, rosemary oil, and spearmint oil; citrus oils such as orange oil, lemon oil, bitter orange oil and tangerine oil; alliaceous flavors: garlic, leek, chive, and onion; botanical extracts: *arnica* flower extract, chamomile flower extract, hops extract, and marigold extract; botanical flavor extracts: blackberry, chicory root, cocoa, coffee, kola, licorice root, rose hips, sarsaparilla root, *sassafras* bark, tamarind and vanilla extracts; protein hydrolyzates: hydrolyzed vegetable protein (HVPs), meat protein hydrolyzates, milk protein hydrolyzates; and compounded flavors both natural and artificial including those disclosed in S. Heath, Source Book of Flavors, Avi Publishing Co. Westport, Conn., pp. 149-277, 1981, which is incorporated herein by reference. The flavor may be in the form of oil, aqueous solution, non-aqueous solution or an emulsion. The flavor may be used singly or in combination.

Although the exact amount of an encapsulate encapsulated in a glass matrix depends, in part, upon the nature of the glassy matrix, and the anticipated end use of the final composition, in one embodiment, the encapsulation composition comprises from 0.01 to 20% by weight, based on the total weight of the composition, of an encapsulate. Preferably, the encapsulation composition comprises from 6 to 12% by weight, based on the total weight of the composition, of an encapsulate. In one embodiment, the encapsulate is a flavor.

When the encapsulate is a lipophilic flavor, the flavor can be dispersed in a glassy matrix with the aid of a surface active carbohydrate in the matrix or with an emulsifier added to the encapsulant or to the matrix blend. Emulsifiers such as distilled monoglycerides, ethoxylated monoglycerides, lactylated monoglycerides, acetylated monoglycerides, diacetyl tartaric acid esters of monoglycerides (D.A.T.E.M.'s), propylene glycol monoesters, sorbitan monostearate, sorbitan tristearate, polyglycerol esters, polyoxyethylene sorbitan monoester and triesters, sucrose esters, sodium stearoyl lactylate (S.S.L.), lecithin, hydroxylated lecithin, oleyl lactylic acid, lactylated esters of monoglycerides, lactylated fatty acid esters of glycerol and propylene glycol, and lactylated esters of propylene glycol monoglycerides, saponins, surface active plant extracts, and the sodium, potassium, calcium, and magnesium salts of fatty acids can be employed singly or in combination. The emulsifier(s) is (are) used at the level of 0.1 to 10% of the selected flavor. In one embodiment, the emulsifier is at least one sorbitan polyoxyethylene monoester.

In addition to the foregoing encapsulates, at least one optional ingredient such as conventionally used in the art, may be included in the encapsulation compositions of one embodiment. For example, colorings, sweeteners, food acids, salts fragrances, diluents, flavor maskers, flavor enhancers, fillers, preservatives, antioxidants, stabilizers, and lubricants may be employed herein, if desired, singly or in combination.

The present encapsulation compositions are prepared by melt extrusion at the moisture content of the melt and product below 12%, by weight of the total encapsulation composition. The glass transition temperature of the composition is above room temperature and is preferably from 25 to 80° C., from 35 to 55° C., from 25 to 50° C., from 30 to 45° C., or from 30 to 40° C. If there is a sufficient amount of water in the matrix components, then no additional plasticizer is added to the blend in the extrusion process.

In the present process, the plasticizer may be liquid or solid, and is any plasticizer which is suitable for facilitating the formation of the melt in the extruder while at the same time affording the encapsulation composition which exists in the glassy state, rather than in viscoelastic state at room temperature. Suitable plasticizers include water; glycerol; propylene glycol: aqueous solutions of glycerol, propylene glycol, monosaccharides, and disaccharides; and invert and high fructose corn syrups, which can be used singly or in combination. In one embodiment, the composition is prepared by using water as a liquid plasticizer.

Suitable carbohydrates which are used as a LMW nonpolymeric component in the formulas and which function in a concomitant fashion as a solid plasticizer include mono- and disaccharides including sucrose, dextrose, trehalose, maltose, invert syrups, molasses; also corn syrups, corn syrup solids 36 to 42 D.E., which can be used singly or in combination. Suitable polyols are erythritol, sorbitol, mannitol, lactitol, maltitol, isomalt, dulcitol, xylitol, hydrogenated corn syrup solids, hydrogenated glucose, maltose, or lactose syrup solids, which can be used singly or in combination. In one embodiment, a carbohydrate is sucrose, maltose, or trehalose, and a polyol is mannitol, maltitol, sorbitol, isomalt, or a mixture thereof.

The plasticizer is added in an amount which results in the formation of a melt in the extruder, while at the same time affording a product which exists in the glassy state at room temperature. Thus, the amount of the added plasticizer may be selected to afford a product which has a Tg of at least 25° C., preferably at least 35° C., and more preferably at least 40° C.

The glassy, crystalline, or partially crystalline components of matrix (B), along with the plasticizer, form a melt in the extruder. Although the mixing action of the extruder will supply heat to the matrix/plasticizer mixture, in one embodiment, additional heat may be supplied to ensure formation of the melt. The additional heat may be supplied in some of the extruder zones or extruders in an assembly while other parts of the assembly would provide cooling to maintain the target temperature profile. The encapsulate (A) may be added to the matrix (B) as a dry blend or may be continuously added as a liquid to the feeding or any other zone of the extruder by injection and mixed with the melted matrix/plasticizer mixture before exiting the extruder. In one preferred embodiment, a flavor is added to the feeding zone of an extruder that performs mixing, melting, and homogenizing functions.

In certain embodiments, an additional emulsifier can be added to the dry blend.

Preferred flavorants may be compounded flavors, essential oils, citrus oils, fruit extracts and essences, oleoresins and other flavorant forms, which can be used singly or in combination. In some cases, the flavors can be diluted in a series of flavor solvents. These include fractionated coconut oils (medium chain triglycerides), propylene glycol, glycerol, and triacetin (glycerol triacetate) among others.

In one embodiment, an extruder assembly equipped with heating and cooling jackets is used. In the heating part there are zones where mixing, melting, and homogenizing is performed. Additional zones may provide cooling, shaping, and actual extrusion of the melt.

When the encapsulation composition exits the extruder, it may be die-face cut, optionally dried, and cooled in ambient or sub-ambient temperature air. For example, cold (5-15° C.) airflow can be used. Although not necessary, the cooled product may be further processed by polishing, coating, sieving, or a combination thereof. The product may also be treated with an anti-caking compound either before or after size reduction.

Other features of the invention will become apparent in the course of the following descriptions of exemplary embodiments which are given only for illustration of the invention and are not intended to be limiting thereof.

EXAMPLES

Extrusion.

Melt extrusion was accomplished utilizing a 2" extrusion assembly equipped with a heating and a cooling jacket, fitted with a liquid injection port in the feeding zone of the assembly and a multi-orifice die. A matrix composition which included pre-blended carbohydrates and other required components was metered into the feed port at a feed rate between 100 to 250 g/min of solids. A liquid plasticizer was injected into the feed zone of the extruder assembly by a metering peristaltic pump at 0-25 ml/min. A liquid flavorant was injected into the feed zone of the extruder assembly by a metering peristaltic pump at 2-30 g/min depending on the application. The heating/cooling jacket temperatures of the extruder assembly were set in the range 170-250° F. After bringing the assembly into a steady-state, the extrudate was die-face cut with a cutter. The uniform particles were collected on a tray and optionally dried and air-cooled.

Analytical Methods

The particle size and shape distribution was characterized with a caliper, by sieve analysis, with Malvern particle size analyzer, and optical microscopy.

A Modulated Differential Scanning Calorimeter (MDSC) Q2000 (TA Instruments) was used to determine glass transition parameters and melt transitions. The modulated mode employed a sinusoidal modulation of linearly increasing temperature. The modulation allowed separation and characterization of glass transition as a reversing process. A heating ramp rate of 5° C./min was employed in combination with +/−1° C. modulation amplitude and 60 s period of modulation. The glass transition temperature was determined as a midpoint of the glass transition temperature interval. The heat capacity change ($\Delta C_p$, J/(g ° C.)) during the step-like glass transition was also measured. The MDSC tests were run in duplicate.

Water content of the matrix blends and final encapsulation compositions was measured by a Karl-Fisher method.

Solubility of particles was evaluated by stirring 0.5 g of the particles in 150 ml of water at 50° F. under constant stirring with a spoon at about 120 spins per minute. Separate samples were evaluated at 5 seconds time intervals. The minimum time required to completely solubilize the particles was reported is the solubility time. The evaluation around the minimum solubility time was performed in duplicate.

Total flavor load and surface oil were determined by solvent extraction of a flavor, followed by GC analysis. Total flavor load was measured as volume of flavor per weight of encapsulation composition and recalculated to weight of flavor per weight of the encapsulation composition, using specific gravity of citrus flavor 0.85 g/ml. Surface oil was measured as weight of flavor extracted from the surface of the particles of encapsulation composition and reported as parts per million (ppm) in relation to total flavor load.

The particle density of the milled extruded strands was measured with a Micromeritics powder pycnometer, model AccuRys 1330 (Micromeritics, Norcross, Ga. 30093), using helium as a filling gas.

Example 1

A matrix composition which included 30% by weight of maltodextrin 18DE (Dextrose Equivalent), 40% of OSAN-modified starch, and 30% maltose was dry blended and fed at a rate of 228 g/min into the extruder assembly. Deionized water was metered into the feed port at 1 g/min. The extruder jacket temperature was maintained at 220-275° F. in the mixing, melting and homogenizing zones, and 190-210° F. in the cooling part of the assembly. Orange Valencia oil (5 fold) was metered into the mix, targeting 10% flavor load by weight. The encapsulation composition was extruded through a 0.031" multi-orifice die, and die-face cut to generate particles. No stringing or clumping of the particles was observed during cutting. The particles were cooled on a tray by chilled air (5-15° C.) to yield a glassy solid.

The resultant solid particles contained 4.3% water, had the glass transition temperature (Tg) 52.7° C., $\Delta C_p$=0.21 J/(g ° C.), and contained 8.5% of the flavor by weight. The solubility time was 55-60 seconds. Surface oil was 294 ppm (0.025%) by weight of total flavor. Particle size distribution measured by sieve analysis was as following: 0% on USS20 (0.84 mm), 9.5% on USS25 (0.71 mm), 76.5% on USS30 (0.6 mm), 13.9% on USS35 (0.5 mm), and 0.1% on the pan. Less than 10% of the particles by weight deviated by their size from the mean value by more than 20% of the mean value.

Example 2

A matrix composition which included 30% by weight of maltodextrin 18DE (Dextrose Equivalent), 40% OSAN-modified starch, and 30% sucrose was dry blended and fed at a rate of 228 g/min into the extruder assembly. Deionized water was metered into the feed port at 5 g/min. The extruder jacket temperature was maintained at 220-275° F. in the mixing, melting and homogenizing zones, and 190-210° F. in the cooling part of the assembly. Orange Valencia oil (5 fold) was metered into the mix, targeting 10% flavor load by weight. The encapsulation composition was extruded through a 0.031" multi-orifice die, and die-face cut to generate particles. No stringing or clumping of the particles was observed during cutting. The particles were cooled on a tray by chilled air (5-15° C.) to yield a glassy solid.

The resultant solid particles contained 3.4% water, had the glass transition temperature (Tg) 52.0° C., $\Delta Cp=0.29$ J/(g °C.), and contained 8.1% of the flavor by weight. The solubility time was 55-60 seconds. Surface oil was 457 ppm (0.046%) by weight of total flavor. Particle size distribution measured by sieve analysis was as following: 0% on USS20 (0.84 mm), 27.9% on USS25 (0.71 mm), 57.4% on USS30 (0.6 mm), 14.5% on USS35 (0.5 mm), and 0.2% on the pan. Less than 10% of the particles by weight deviated by their size from the mean value by more than 23% of the mean value.

Example 3

A matrix composition which included 30% by weight of maltodextrin 18DE (Dextrose Equivalent), 40% OSAN-modified starch, and 30% trehalose dihydrate was processed under conditions of the Example 1. No stringing or clumping of the particles was observed during cutting.

The resultant solid particles contained 5.1% water, had the glass transition temperature (Tg) 48.3° C., $\Delta Cp=0.1$ J/(g °C.), and contained 9.0% of the flavor by weight. The solubility time was 55-60 seconds. Surface oil was 160 ppm (0.016%) by weight of total flavor. Particle size distribution measured by sieve analysis was as following: 0% on USS20 (0.84 mm), 4.5% on USS25 (0.71 mm), 68.1% on USS30 (0.6 mm), 27.0% on USS35 (0.5 mm), and 0.2% on the pan. Less than 10% of the particles by weight deviated by their size from the mean value by more than 10% of the mean value.

Comparative Example 4

A matrix composition which included 30% by weight of maltodextrin 18DE (Dextrose Equivalent), 40% of OSAN-modified starch, and 30% dextrose anhydrous was dry blended and fed at a rate of 228 g/min into the extruder assembly. Deionized water was metered into the feed port at 1 g/min. The extruder jacket temperature was maintained at 200-250° F. in the mixing, melting and homogenizing zones, and 180-200° F. in the cooling part of the assembly. Lemon oil (single fold) was metered into the mix, targeting 10% flavor load by weight. The encapsulation composition was extruded through a 0.031" multi-orifice die, and die-face cut to generate particles. Particles were moderately stringing during cutting with about 50% of the particles forming strings or clumps. The trial was considered a failure as no acceptable product was generated.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A particulate extrusion encapsulation composition in a glassy state, which is 1) soluble in aqueous systems within 15 seconds to 3 minutes under stirring or mixing, 2) has a level of an encapsulate on the surface of the particles of less than 1% based on the weight of the encapsulate, 3) has a narrow particle size and shape distribution, where each characteristic dimension of 90% of the particles by weight does not deviate by more than 30% from the mean value of that characteristic dimension; said composition comprising:
   (A) the encapsulate, encapsulated in (B) a glassy matrix comprising one or more matrix components, and one or more plasticizers;
      wherein said glassy matrix (B) comprises: 10-50% of at least one low molecular weight material selected from the group consisting of sugar, polyol, corn syrup solids, organic acid and a salt of an organic acid; 0 to 60% of at least one modified starch, and 0 to 60%, based on the total weight of said glassy matrix (B), of at least one material selected from the group consisting of maltodextrin, inulin; gum Arabic, larch gum, gelatin, hydrolyzed gelatin, dextrin, and hydrogenated starch hydrolysate,
   wherein the encapsulate (A) is present in the extrusion encapsulation composition in an amount of from 4% to 20% by weight, based on the total weight of the extrusion encapsulation composition;
   and wherein the glassy matrix (B) comprises at least one anti-sticking agent of a calcium or magnesium salt of a fatty acid, and wherein the anti-sticking agent is present in an amount up to 3%;
   wherein said extrusion encapsulation composition is prepared by a process comprising:
      (i) mixing the matrix components of the glassy matrix (B), the encapsulate (A), and the plasticizer, thereby obtaining a blend;
      (ii) in at least one extruder, melting the blend, dispersing the encapsulate in the melted blend to form a viscous dispersion, and cooling the viscous dispersion in the extruder or in a combination of extruders;
      (iii) shaping, extruding and die-face cutting said viscous dispersion, thereby obtaining said extrusion encapsulation composition, wherein said encapsulate (A) is encapsulated in the glassy matrix (B),
      (iv) optionally drying the extruded encapsulation composition, and
      (v) further cooling the encapsulation composition.

2. The composition of claim 1, wherein the extrusion encapsulation composition is stable against caking or clumping in a sealed packaging for at least six month at ambient temperature.

3. The composition of claim 1, wherein the particles of the extrusion encapsulation composition have an average particle size in the range of from 0.1 mm to 7 mm.

4. The composition of claim 1, wherein the particles of the extrusion encapsulation composition have an average particle size in the range from 0.3 mm to 3 mm.

5. The composition of claim 1, which has a glass transition temperature of from 25° C. to 80° C.

6. The composition of claim 1, which is soluble in water, water-ethanol mixtures, and other aqueous solutions.

7. The composition of claim 1, wherein the composition is soluble in an aqueous system within 15 seconds to 2 minutes under stirring or mixing.

8. The composition of claim 1, wherein less than 0.1% of the encapsulate (A) is present on the surface of the particles of the extrusion encapsulation composition, based on the total weight of the encapsulate (A).

9. The composition of claim 1, where the particles have a similar shape and each characteristic dimension of 90% of the particles by weight does not deviate by more than 30% from the mean value of that characteristic dimension.

10. The composition of claim 7, where each characteristic dimension of 90% of the particles by weight does not deviate by more than 20% from the mean value of that characteristic dimension.

11. The composition of claim 1, wherein the at least one low molecular weight sugar is at least one sugar selected from the group consisting of maltose, trehalose, dextrose, lactose, fructose, xylose, and sucrose.

12. The composition of claim 1, wherein at least one modified starch is at least one n-octenylsuccinic acid anhydride modified starch (OSAN-starch).

13. The composition of claim 1, comprising 20 to 40% by weight, based on the total weight of said glassy matrix (B) of at least one selected from the group consisting of maltose, trehalose, dextrose, lactose, fructose, xylose, and sucrose; 0 to 60% of at least one modified starch; and 0 to 60%, based on the total weight of said glassy matrix (B), of at least one maltodextrin, inulin, gum Arabic, larch gum, gelatin, hydrolyzed gelatin, dextrin, hydrogenated starch hydrolyzate.

14. The composition of claim 1, wherein said encapsulate is at least one component selected from the group consisting of a flavor, a fragrance, a vitamin, a dietary supplement, and a medication.

15. The composition of claim 1, wherein said encapsulate is a flavor.

16. The composition of claim 13, wherein said encapsulate is a flavor.

17. The composition of claim 15, wherein said flavor is at least one flavor selected from the group consisting of a natural flavor, a natural extract, an oleoresin, an essential oil, a protein hydrolyzate, a reaction flavor, an artificial flavor, and a compounded flavor.

18. The composition of claim 1, wherein said plasticizer is at least one plasticizer selected from the group consisting of water, glycerin, propylene glycol, and a carbohydrate solution.

19. The composition of claim 18, wherein the components of the glassy matrix (B) comprise water, and wherein the extrusion encapsulation composition is obtained by a process in which water is not directly added to the composition during the mixing.

20. The composition of claim 1, where the glassy matrix (B) further comprises up to 5% of at least one emulsifier.

21. The composition of claim 1, where the encapsulate (A) further comprises up to 10% of at least one emulsifier.

22. The composition of claim 1, wherein said aqueous system is an aqueous solution, a beverage, a sauce, dough, a chewing gum, or any other system containing water or exposed to water in processing, in a final application, or during chewing and mastication.

23. The composition of claim 1, wherein such composition is soluble in an aqueous system within 15 seconds to 1 minute under stirring or mixing.

24. The composition of claim 1, wherein said shaping and extruding is performed by forcing the viscous dispersion through a die, followed by die-face cutting the dispersion with a cutter to form particles.

25. The composition of claim 1, wherein the particles are dried and cooled after the shaping, extruding and die-face cutting.

26. A food system containing the extrusion encapsulation composition of claim 1.

27. A shaped, solid particulate extrusion encapsulation composition, which has a narrow particle size and shape distribution, comprising:
(A) the encapsulate, encapsulated in (B) a solid matrix comprising one or more matrix components, and one or more plasticizers;
wherein said solid matrix (B) comprises: 0-50% of at least one low molecular weight material selected from the group consisting of sugar, polyol, corn syrup solids, organic acid and a salt of an organic acid; 5 to 100% of at least one material selected from the group consisting of carbohydrate, protein, spice, herb, vegetable powder, and a fruit powder,
wherein the encapsulate (A) is present in the extrusion encapsulation composition in an amount of from 0.1% to 20% by weight, based on the total weight of the extrusion encapsulation composition;
and wherein the glassy matrix (B) comprises at least one anti-sticking agent of a calcium or magnesium salt of a fatty acid, and wherein the anti-sticking agent is present in an amount up to 3%;
wherein said extrusion encapsulation composition is prepared by a process comprising:
(i) mixing the matrix components of the solid matrix (B), the encapsulate (A), and the plasticizer, thereby obtaining a blend;
(ii) in at least one extruder, melting the blend, dispersing the encapsulate in the melted blend to form a viscous dispersion, and cooling the viscous dispersion in the extruder or in a combination of extruders;
(iii) shaping, extruding and die-face cutting said viscous dispersion, thereby obtaining said shaped, extrusion encapsulation composition, wherein said encapsulate (A) is encapsulated in the solid matrix (B),
(iv) optionally drying the extruded encapsulation composition, and
(v) further cooling the encapsulation composition.

28. The shaped, solid particulate extrusion encapsulation composition of claim 27, wherein the particles have a shape selected from the group consisting of a letter, a logo, a digit, and a familiar food shape.

29. A particulate extrusion encapsulation composition in a glassy state, which is 1) soluble in aqueous systems within 15 seconds to 3 minutes under stirring or mixing, 2) has a level of an encapsulate on the surface of the particles of less than 1% based on the weight of the encapsulate, 3) has a narrow particle size and shape distribution, where each characteristic dimension of 90% of the particles by weight does not deviate by more than 30% from the mean value of that characteristic dimension; said composition comprising:
(A) the encapsulate, encapsulated in (B) a glassy matrix comprising one or more matrix components, and one or more plasticizers;
wherein said glassy matrix (B) comprises: 10-50% of at least one low molecular weight material selected from the group consisting of sugar, polyol, corn syrup solids, organic acid and a salt of an organic acid; 0 to 60% of at least one modified starch, and 30% to 60%, based on the total weight of said glassy matrix (B), of maltodextrin, dextrin, and hydrogenated starch hydrolysate, wherein the encapsulate (A) is present in the extrusion encapsulation composition in an amount of from 4% to 20% by weight, based on the total weight of the extrusion encapsulation composition;

and wherein the glassy matrix (B) comprises at least one anti-sticking agent of a calcium or magnesium salt of a fatty acid, and wherein the anti-sticking agent is present in an amount up to 3%;

wherein said extrusion encapsulation composition is prepared by a process comprising:

(i) mixing the matrix components of the glassy matrix (B), the encapsulate (A), and the plasticizer, thereby obtaining a blend;

(ii) in at least one extruder, melting the blend, dispersing the encapsulate in the melted blend to form a viscous dispersion, and cooling the viscous dispersion in the extruder or in a combination of extruders;

(iii) shaping, extruding and die-face cutting said viscous dispersion, thereby obtaining said extrusion encapsulation composition, wherein said encapsulate (A) is encapsulated in the glassy matrix (B), (iv) optionally drying the extruded encapsulation composition, and (v) further cooling the encapsulation composition.

* * * * *